(12) United States Patent
Geenty (10) Patent No.: US 8,651,857 B2
(45) Date of Patent: Feb. 18, 2014

(54) DENTAL APPLIANCE

(75) Inventor: Joseph Geenty, Wollongong (AU)

(73) Assignee: Clearsmile Holdings Pty Limited, Wollongong, NSW (AU)

( * ) Notice: Subject to any disclaimer, the term of this patent is extended or adjusted under 35 U.S.C. 154(b) by 0 days.

(21) Appl. No.: 12/744,214

(22) PCT Filed: Nov. 10, 2008

(86) PCT No.: PCT/AU2008/001665
§ 371 (c)(1),
(2), (4) Date: Jul. 7, 2010

(87) PCT Pub. No.: WO2009/067731
PCT Pub. Date: Jun. 4, 2009

(65) Prior Publication Data
US 2010/0266975 A1    Oct. 21, 2010

(30) Foreign Application Priority Data

Nov. 27, 2007 (AU) .............................. 2007906489

(51) Int. Cl.
*A61C 7/08* (2006.01)
(52) U.S. Cl.
USPC ............................................................ 433/6
(58) Field of Classification Search
USPC ........................................ 433/6, 18, 24, 215
See application file for complete search history.

(56) References Cited

U.S. PATENT DOCUMENTS

| 2,479,780 | A | * | 8/1949 | Remensnyder | 433/6 |
| 5,163,840 | A | | 11/1992 | Bourke | |
| 5,692,894 | A | * | 12/1997 | Schwartz et al. | 433/6 |
| 5,876,199 | A | | 3/1999 | Bergersen | |
| 6,244,861 | B1 | | 6/2001 | Andreiko | |
| 6,524,101 | B1 | | 2/2003 | Phan et al. | |
| 6,830,450 | B2 | * | 12/2004 | Knopp et al. | 433/6 |
| 2003/0219690 | A1 | | 11/2003 | Graham | |
| 2003/0224311 | A1 | | 12/2003 | Cronauer | |
| 2006/0177789 | A1 | * | 8/2006 | O'Bryan | 433/6 |
| 2006/0188834 | A1 | * | 8/2006 | Hilliard | 433/24 |

FOREIGN PATENT DOCUMENTS

| CA | 2346784 A1 | 4/2000 |
| CA | 2688867 A1 | 10/2003 |
| WO | 9410935 | 5/1994 |
| WO | 2004004592 | 1/2004 |
| WO | 2005-092234 A1 | 10/2005 |

OTHER PUBLICATIONS

International Preliminary Report on Patentability for PCT/AU2008/001665 completed Nov. 23, 2009.

(Continued)

*Primary Examiner* — Ralph Lewis
(74) *Attorney, Agent, or Firm* — Barnes & Thornburg LLP (57) ABSTRACT

A dental appliance for correcting tooth alignment. The appliance includes a body for seating on an arch of teeth. The body is at least partially elastically deformable and has a seated condition into which it is elastically deformable to be seated on an arch of teeth. The body is constructed, when seated on an arch of teeth, for applying, by virtue of said elastic deformation, a correction force on one or more misaligned teeth, at or adjacent a base of the crown of each misaligned tooth, in a direction in which each misaligned tooth is to be moved to correct its alignment.

22 Claims, 3 Drawing Sheets

(56) References Cited

OTHER PUBLICATIONS

International Search Report for PCT/AU2008/001665 completed Feb. 3, 2009.
Curry, et al., Integrated Three-Dimensional Craniofacial Mapping at the Craniofacial Research Instrumentation Laboratory/University of the Pacific, Seminars in Orthodontics, vol. 7, No. 4 (Dec. 2001); pp. 258-265, 8 pages.
Hans, et al., Three-Dimensional Imaging: The Case Western Reserve University Method, Seminars in Orthodontics, vol. 7, No. 4 (Dec. 2001): pp. 233-243, 11 pages.
Wong, Benson H., DDS, Invisalign A to Z, Techno Bytes, American Journal of Orthodontics and Dentofacial Orthopedics, vol. 121, No. 5, pp. 540-541, 2 pages.
European Search Report for EP 11007523.1, dated Nov. 7, 2011.

\* cited by examiner

DENTAL APPLIANCE

CROSS REFERENCE TO RELATED APPLICATIONS

This application is the U.S. national phase of PCT/AU2008/001665 filed Nov. 10, 2008. PCT/AU2008/001665 claims benefit under the Paris Convention to AU 2007906489 filed Nov. 27, 2007. The disclosures of both of AU 2007906489 and PCT/AU2008/001665 are hereby incorporated herein by reference.

TECHNICAL FIELD

The present invention generally relates to a dental appliance and, more particularly, to a dental appliance for correcting tooth alignment, and to a set of such appliances. The invention relates also to a method of forming a dental appliance for correcting tooth alignment, and to a method of correcting tooth alignment.

BACKGROUND OF THE INVENTION

Dental or orthodontic appliances such as braces are known for correcting tooth alignment. These appliances are, however, regarded by many patients, especially adults, as unsightly.

A known alternative to braces comes in the form of a removable appliance which, in the general fashion of a mouthguard, is received over an arch of teeth of a patient. An appliance of the type in question is at least partially elastically deformable, being constructed to be elastically deformed when received over an arch of teeth including a misaligned tooth or teeth, so that, by virtue of the elastic deformation, the appliance applies correction forces on a misaligned tooth or teeth. These type of appliances are of transparent construction, so that they have little or no obvious adverse aesthetic effects on the appearance of a patient.

However, because of the material from which these appliances are constructed, corrective movement of a tooth by a single appliance is limited, so that a great number of sequential appliances (e.g. 40) are required to correct tooth alignment, especially in cases where significant alignment correction is required. Another disadvantage of these type of appliances is that their construction is of such a nature that they do not naturally properly seat on an arch of teeth. When an appliance in question is forced to seat properly on an arch of teeth, it, on the one hand, may lead to damage of the appliance and, on the other hand, may cause discomfort to a patient and/or cause tissue and/or tooth damage. For example, excessive force applied to a tooth by means of an appliance in question may result in root resorption or, in some cases, may restrict blood supply to the tooth, which adversely affects the vitality of the tooth with consequential discolouration of the tooth.

OBJECT OF THE INVENTION

It is the object of the present invention to substantially overcome or at least ameliorate one or more of the above disadvantages, or at least to provide a useful alternative.

SUMMARY OF THE INVENTION

In accordance with a first aspect, the present invention provides a dental appliance for correcting tooth alignment, the appliance including a body for seating on an arch of teeth, the body being at least partially elastically deformable and having a seated condition into which it is elastically deformable to be seated on an arch of teeth, and the body being constructed, when seated on an arch of teeth, for applying, by virtue of said elastic deformation, a correction force on one or more misaligned teeth, at or adjacent a base of the crown of each misaligned tooth, in a direction in which each misaligned tooth is to be moved to correct its alignment.

Preferably, the body of the appliance is provided with a recess for receiving teeth, the body having a pre-seated condition from which it is elastically deformable into said seated condition, and the recess, when the body is in its pre-seated condition, providing accommodation for a misaligned tooth in a required post-alignment position and for at least part of the misaligned tooth in a pre-alignment position.

Preferably, when the body is in its seated condition its recess provides for simultaneous accommodation of a misaligned tooth in its required post-alignment position and in its pre-alignment position.

The body of the appliance is, preferably, constructed such that when it is in its seated condition, its recess provides for simultaneous accommodation of the entire crown of each misaligned tooth both in its pre-alignment position and its required post-alignment position. The appliance is thus associated only with crowns of teeth.

The appliance is removable. Preferably, the appliance is at least partially transparent. Conveniently, the entire appliance is transparent. Thus, the appliance will not be obviously visible when worn by a patient.

As the appliance is intraoral in nature, it is to be appreciated that the material from which it is constructed is suitable for intraoral use.

The appliance is preferably constructed such that the recess of its body accommodates all, or at least a majority of, the teeth in an arch.

The recess of the body is preferably shaped such that when the body is in both its pre-seated condition and its seated condition, it accommodates each tooth whose alignment does not require correction in the current position of the tooth. The body of the appliance will thus, when seated on teeth of an arch, anchor against teeth whose alignment do not require correction.

Preferably, the body of the appliance is generally in the form of a shell which, when seen in outline in plan view, follows the general outline of an arch of teeth. Preferably, the body is in the form of a relatively thin-walled shell, following the contours of the teeth in an arch.

By virtue of its aforedescribed construction, the body of the appliance, when seen in cross-section, is roughly U shaped, when to be used in relation to an upper arch of teeth, or roughly inverted U-shaped, when to be used in relation to a lower arch of teeth. The body thus preferably includes a lingual portion associated with lingual surfaces of teeth, a facial portion associated with facial surfaces of teeth, and a connecting portion associated with tips, i.e. cusps in the case of molars or pre-molars, of teeth, the connecting portion connecting the lingual portion and the facial portion together. When the body of the appliance is deformed from its pre-seated condition to its seated condition, a part or parts of the lingual portion and/or the facial portion of the body associated with misaligned teeth will be elastically deformed away from the other one of the lingual portion and the facial portion about the connecting portion. That part of the connecting portion associated with each misaligned tooth is preferably wide enough simultaneously to cover the tip of each misaligned tooth when the tooth is in its pre-alignment position and its required post-alignment position, thereby permitting proper seating of the appliance on an arch of teeth including misaligned teeth.

In use, with the appliance seated on an arch of teeth, the alignment force applied by the appliance on each misaligned tooth will thus be applied, by said one of the lingual portion and the facial portion of the body which has been elastically deformed, on the tooth at or adjacent the base of the crown of the tooth. This, in the case of translational movement, i.e. movement in a lingual or facial direction, of a tooth, ensures bodily movement of the tooth, as opposed to tipping of the tooth.

As foreshadowed above, an appliance according to this aspect of the invention can be used in relation to an upper or a lower arch of teeth.

It is to be appreciated that the appliance can be used to effect both translational corrective movement, rotational corrective movement (i.e. movement about a longitudinal axis of the tooth), lateral corrective movement, vertical upwards corrective movement, and vertical downward corrective movement of a tooth, or a combination of movements.

In accordance with a second aspect, the present invention provides a dental appliance for correcting tooth alignment, the appliance including an elastically deformable body having a lingual portion and a facial portion, the lingual portion and the facial portion generally opposing each other, with one of the lingual portion and the facial portion being elastically deformable away from the other one of the lingual portion and the facial portion to permit seating of the body on an arch of teeth having one or more misaligned teeth with the teeth in the arch being received between the two portions, so that in use the elastically deformed portion of the body applies a correction force on at least one misaligned tooth in the arch in a direction towards the other one of the lingual portion and the facial portion, said deformable portion of the body being constructed such that a correction force applied thereby on a lower portion of the crown of said misaligned tooth exceeds a force applied on an upper part of the crown of the misaligned tooth.

In accordance with a third aspect, the present invention provides a dental appliance for correcting tooth alignment, the appliance including a body for seating on an arch of teeth having one or more misaligned tooth, the body being constructed to be elastically deformed when seated on the arch of teeth and, by virtue of said elastic deformation, to apply a correction force on at least one misaligned tooth in the arch for moving the misaligned tooth, the appliance being constructed for effecting movement of up to about 1 mm of said at least one misaligned tooth.

In accordance with a fourth aspect, the present invention provides a dental appliance for correcting tooth alignment, the appliance including an elastically deformable body for seating on an arch of teeth having at least one misaligned tooth, the body being constructed to be elastically deformed when seated on an arch of teeth, and when seated on the arch for applying, by virtue of said elastic deformation, a greater correction force on a lower part of the crown of at least one misaligned tooth in the arch than on an upper part of the crown of the misaligned tooth.

In accordance with a fifth aspect, the present invention provides a dental appliance for correcting tooth alignment, the appliance including an elastically deformable body for seating on an arch of teeth having at least one misaligned tooth, the body being constructed to be elastically deformed when seated on an arch of teeth, and when seated on the arch for applying, by virtue of said elastic deformation, a correction force on at least one misaligned tooth in the arch on a lower part of the crown of the misaligned tooth, for moving the misaligned tooth.

In accordance with a sixth aspect, the present invention provides a set of appliances for correcting tooth alignment, the set including a plurality of appliances as hereinbefore described, each having a pre-seated condition and a seated condition, to be used in series for incrementally correcting tooth alignment.

Preferably, the appliances of the set are shaped such that the pre-seated condition of the body of one appliance, as far as accommodation of a lower part or base of the crown of each misaligned tooth by its recess is concerned, substantially corresponds with the seated condition of the body of the succeeding appliance in the set.

In accordance with the seventh aspect, the present invention provides a method of forming an appliance for correcting tooth alignment, the appliance including a body for seating on an arch of teeth, the method including:

manipulating a three-dimensional representation of an arch of teeth in pre-alignment positions to include also a required post-alignment position of each misaligned tooth in the arch; and forming the appliance based on the manipulated three-dimensional representation of the teeth in the arch, wherein the body of the appliance is provided with a recess for receiving teeth, the recess providing accommodation for a misaligned tooth in its required post-alignment position and for at least part of the misaligned tooth in a pre-alignment position.

Preferably, manipulation of the three-dimensional representation include discarding part of each misaligned tooth, so that the manipulated representation represents part of each misaligned tooth in its pre-alignment position and the entire misaligned tooth in its post-alignment position. Preferably, the manipulated model will include an upper part of each misaligned tooth in its misaligned position.

The method, prior to said manipulation of the three-dimensional representation, preferably includes creating the three-dimensional representation of the teeth in the arch in their pre-alignment positions. The three-dimensional representation can be created by making use of photographs, X-rays, and the like. The three-dimensional representation can be created digitally, so that it is in the form of a computer simulated model, or it can be created manually, so that it is in the form of a physical model.

When a set of appliances is to be formed, the method preferably, after forming of each individual appliance, includes manipulating the three-dimensional representation.

In accordance with an eighth aspect of the invention, there is provided a method of correcting tooth alignment, the method including applying a correction force by means of an elastically deformable tooth alignment appliance on a lower part of the crown of a misaligned tooth.

Naturally, the correction force will be applied to the misaligned tooth in a direction in which the tooth is to be moved to correct its alignment. Thus, the misaligned tooth will be moved from a pre-aligned position to a post-aligned position.

The method, in one embodiment, includes simultaneously correcting alignment of more than one tooth.

In accordance with a ninth aspect, the present invention provides a method of correcting tooth alignment, the method including using an appliance as hereinbefore described.

BRIEF DESCRIPTION OF THE DRAWINGS

A preferred embodiment of the present invention will now be described, by way of example only, with reference to the accompanying schematic drawings wherein.

DETAILED DESCRIPTION OF THE PREFERRED EMBODIMENTS

With reference to the drawings, an embodiment of an appliance for correcting tooth alignment is generally designated by reference numeral 20. The appliance 20, as will be described further hereunder, is a removable appliance which in use seats on an arch of teeth in the general fashion of a mouthguard, and employs elasticity to correct misalignment of teeth. As will become more apparent hereunder, the appliance 20 is custom made in accordance with a particular set of teeth whose alignment requires correction.

The appliance 20 comprises an elongated body 22 defining a recess 24 for accommodating teeth when the appliance 20 is seated on an arch of teeth.

Figure 1:
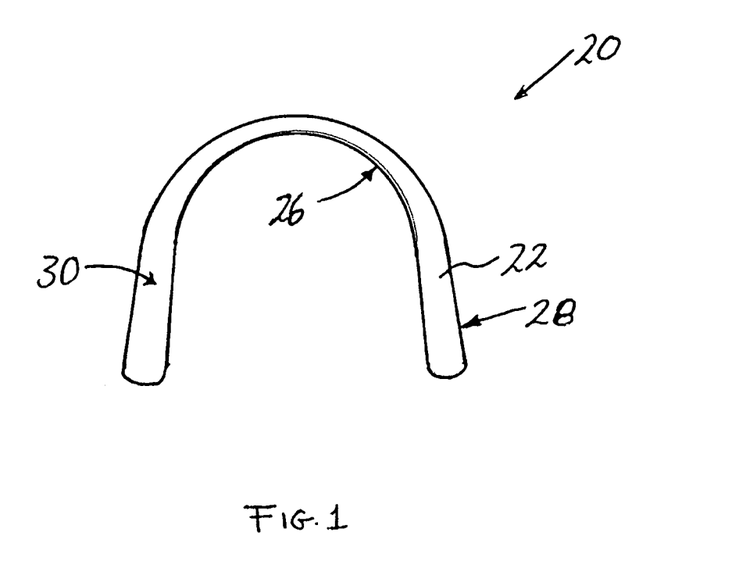
FIG. 1 is a top plan view of an embodiment of an appliance for correcting tooth alignment.

The body 22 of the appliance 20 is generally in the form of a transparent thin-walled shell which is shaped such that when seen in outline in plan view (FIG. 1), it follows the general profile of an arch of teeth. Although the appliance is shown schematically in the drawings, it will in practise be contoured such that it follows the contours of the teeth in an arch. In this regard, it is to be appreciated that the body 22, when seen in outline in cross-sectional view, will in practise, by virtue of the shape of the profiles of teeth, be generally U-shaped where it is associated with posterior teeth, and generally V-shaped where it is associated with anterior teeth.

The body 22 includes a lingual portion 26, a facial portion 28 and a connecting portion 30 connecting the lingual portion 26 and the facial portion 28 together. The various portions 26, 28, 30 are integrally formed with each other, so that the appliance 20 is of unitary construction. The recess 24 of the body 22 is thus defined between the lingual portion 26, the facial portion 28 and the connecting portion 30. The illustrated embodiment of the appliance 20 is to be used in the context of a lower arch of teeth, so that the connecting portion 30 defines an upper end or roof of the body 22, with a lower end of the body 22, i.e. that end defined between free ends of the lingual portion 26 and the facial portion 28, being open to provide for receipt of teeth into the recess 24. An interior face of the body 22, i.e. that face thereof facing into the recess 24, subject to what is said below, generally follows the contours of the teeth in an arch. Thus, contrary to the illustrations, the body 22 of the appliance 20 will be smoothly contoured.

Figure 3:
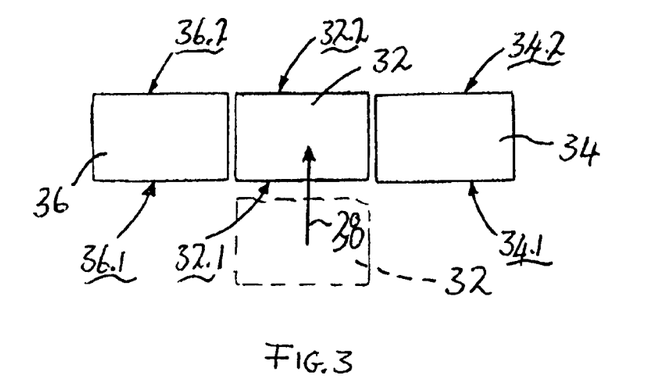
FIG. 3 is a top plan view of part of a lower arch of teeth of a patient.
Figure 4:
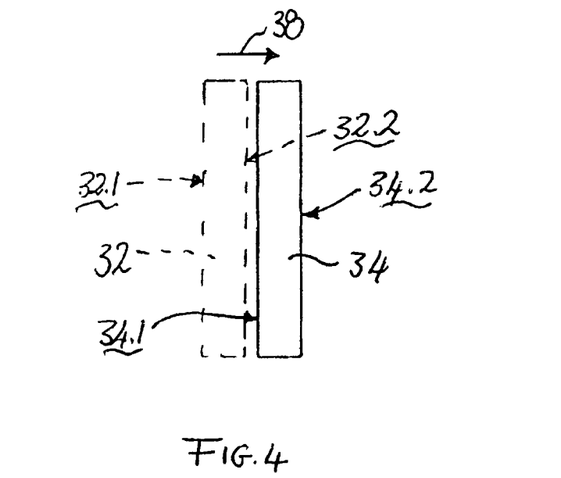
FIG. 4 is a side elevation of the arch of teeth shown in FIG. 3.

Turning now to FIGS. 3 and 4 of the drawings, two central lower teeth 32, 34 and one lateral lower tooth 36 of a patient are shown in top plan view and in side elevation. Only the crowns of the teeth are shown in these figures, and the gums of the patient are also omitted from these figures. The same applies to the other figures in which the teeth 32, 34, 26 are shown. The central tooth 32, which is misaligned, is shown in broken lines in the drawings in a pre-alignment position, and is shown in full lines in a post-alignment position. The misaligned tooth 32 has a lingual surface 32.1, facing towards an interior of the patient's mouth, and a facial surface 32.2, facing towards the exterior of the patient's mouth. Likewise, the teeth 34 and 36 have lingual and facial surfaces which are respectively designated by reference numerals 34.1, 34.2 and 36.1, 36.2. The lingual portion 26 of the body 22 is associated with the lingual portions 32.1, 34.1, 36.1 of the teeth 32, 34, 36, and the facial portion 28 is, in turn, associated with the facial portions 32.2, 34.2, 36.2 of the teeth 32, 34, 26. As can be seen, alignment of the tooth 32 needs to be corrected in relation to the teeth 34, 36 by movement of the tooth 32 in an outward or facial direction, which direction is indicated by arrow 38.

Figure 2:
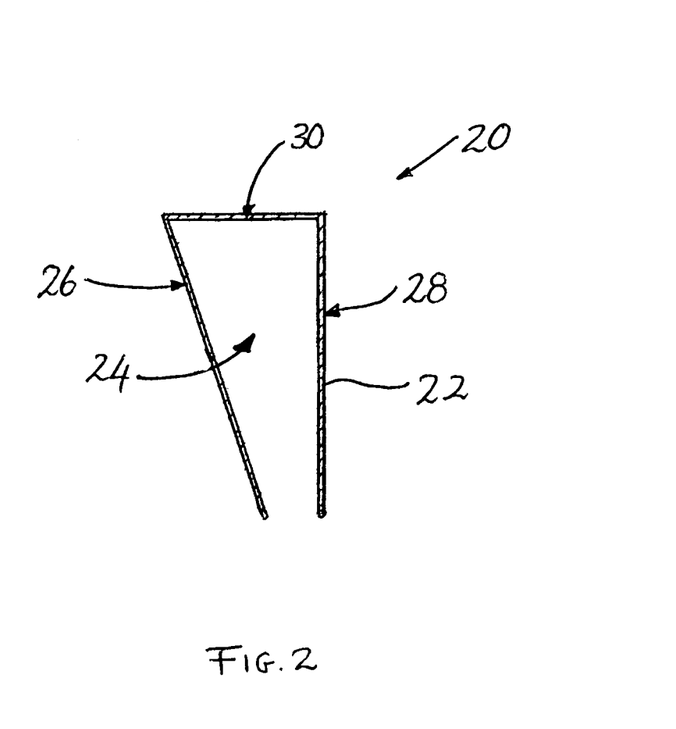
FIG. 2 is a partial cross-sectional view of the appliance shown in FIG. 1.
Figure 6:
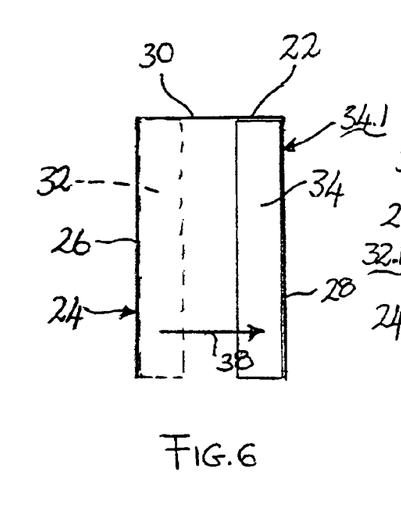
FIGS. 6-10 are partial cross-sectional views of the appliance in accordance with the invention at various stages during correction of alignment of the teeth shown in FIG. 3.
Figures 7, 8, 9, 10:
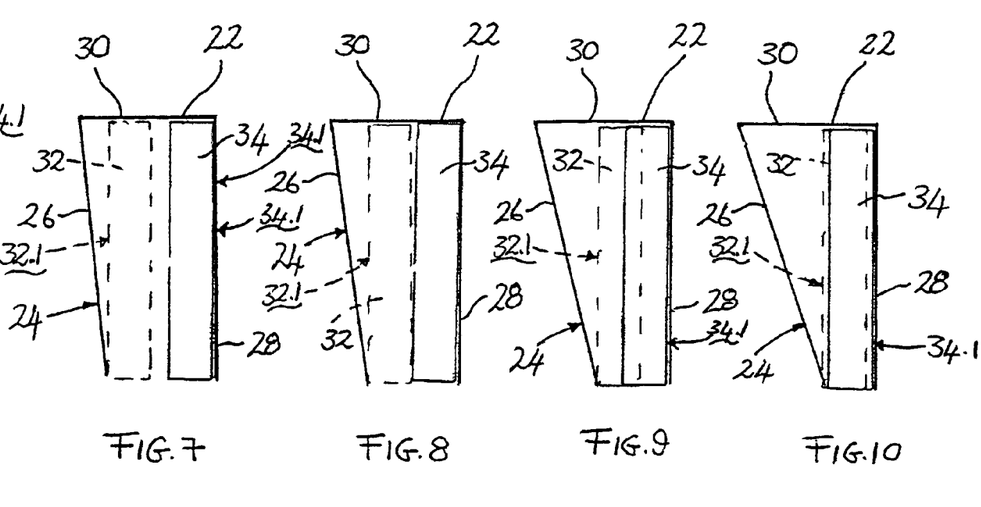

The appliance 20 is constructed of a material which is suitable for intraoral use and, as foreshadowed above, is at least partially elastically deformable. In particular, in the illustrated example, at least the lingual portion 26, where it is, along the length of the body 22, associated with the misaligned tooth 32 is elastically deformable. By virtue of said elasticity, the body 22 has a pre-seated condition (FIGS. 2, 5 and 10), from which pre-seated condition it, in particular in this example the lingual portion 26 thereof, is elastically deformable to a seated condition (FIG. 6) to permit, as described further hereunder, proper seating of the appliance on an arch of teeth. In its pre-seated condition (see in particular FIG. 5), the recess 24 of the body 22 simultaneously provides accommodation for the misaligned tooth 32 in its post-alignment position and for at least the tip part of the crown of the tooth 32 in its pre-alignment position. The connecting portion of the body 22 is thus wide enough simultaneously to cover, in this case bridge, the tip of the tooth 32 both with the tooth in its pre-alignment and its post-alignment positions. The lingual portion 26 of the body 22, when the body 22 is in its pre-seated position, slants operatively downwardly towards the facial portion 28. To deform the body 22 into its seated condition, the lingual portion 26 is deformed about the connecting portion 30. The aforedescribed open lower end of the body 22 is thus widened upon deformation of the body 22 towards its seated condition.

Figure 5:
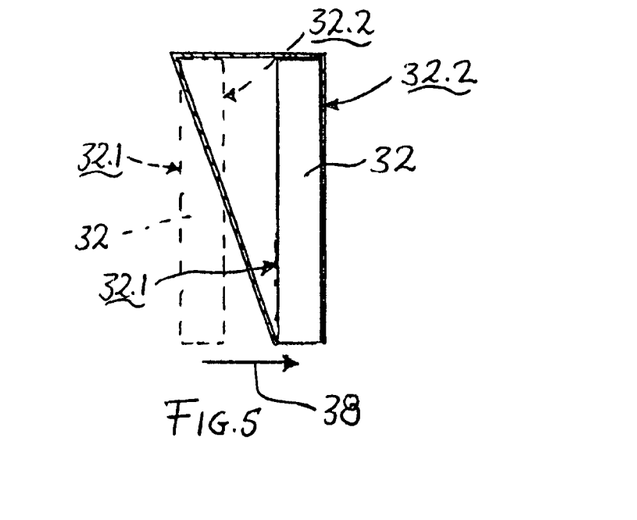
FIG. 5 is a partial cross-sectional view of the appliance shown in FIGS. 1 and 2 superimposed over a side elevation of the teeth shown in FIG. 3.

Turning now in particular to FIG. 5, when forming the appliance 20, both the pre-alignment position (shown in broken lines) of the misaligned tooth 32, as well as the post-alignment position (shown in full lines), i.e. a required aligned position, are taken into account. In particular, when forming the appliance 20, a three-dimensional representation of teeth in an arch is created, each tooth being represented in its present position, i.e. in the case of a misaligned tooth its pre-alignment position. The three-dimensional representation is then manipulated to include also a representation of each misaligned tooth in the arch in a post-alignment position, and to discard or exclude a lower part of each misaligned tooth in its pre-alignment position. The post-alignment position of a misaligned tooth, depending on the degree of alignment required, can be a final required position of the misaligned tooth, or can be an intermediate aligned position. The body 22 of the appliance is then formed such that its recess 24, when the body is in its pre-seated condition (as shown in FIG. 5), provides space for simultaneously accommodating the tip of the crown of the misaligned tooth 32, in its pre-alignment position, as well as the entire tooth 32 in its post-alignment position, and such that when the body 22 is in its seated condition, its recess 24 provides accommodation for the entire crown of the tooth 32 in both its pre-alignment and its post-alignment positions.

In one embodiment the manipulated three-dimensional representation is in the form of a physical model, the model serving as a negative for forming the appliance 20. In another embodiment, the manipulated three-dimensional representation is in the form of a digital model, i.e. a computer simulated model, which is then used to form the appliance 20.

In use, as is illustrated in FIGS. 6-10, the body 22 of the appliance 20 is deformed to its seated condition when the body 22 is seated on teeth of a lower arch. As can be seen in particular in FIG. 6 and as briefly mentioned above, the elastic construction of the body 22 is such that, with the body 22 in its seated condition, the recess 24 thereof accommodates the misaligned tooth 32 in its pre-alignment condition, whilst simultaneously still providing a space for accommodating the tooth 32 in a post-alignment position, which space is progressively occupied by the tooth 32 as its alignment is being corrected. With the body 22 of the appliance 20 in its seated condition, and being seated on the teeth on a lower arch, the facial portion 28 of the body 22 engages the facial surfaces 34.2, 36.2 of the teeth 34, 36. In turn, the lingual portion 26 engages and applies, by virtue of said elastic deformation, an alignment force, in the direction of arrow 38, on the lingual surface 32.1 of the tooth 32, in particular at or adjacent the base of the crown of the tooth 32, for moving the tooth 32 towards its required post-alignment position. When the body 22 is deformed from its pre-seated condition to its seated condition, an enclosed angle formed between the lingual portion 26 and the connecting portion 30 increases. As the body returns to its pre-seated condition as the tooth 32 is moved towards its post-alignment condition, said enclosed angle decreases.

By virtue of the correction force being applied on the tooth 32 at or adjacent the base of its crown, the tooth 32 is bodily moved as its alignment is being corrected, as opposed to tipping of the tooth 32 which may result from a greater alignment force being applied to the a tooth at or adjacent its tip.

Depending upon the extent of misalignment of a tooth, a series of appliances 20, each providing for incremental movement of a misaligned tooth, may need to be used. In this regard, it is envisaged that movement of a tooth of up to 1 mm can be attained by a single appliance 20. In such a set, the appliances 20 will be shaped such that the pre-seated condition of the body 22 of one appliance 20, as far as accommodation of a lower part or base of the crown of each misaligned tooth by its recess 24 is concerned, substantially corresponds with the seated condition of the body 22 of a successive appliance 20 of the set, i.e. an appliance 20 to be used after said one appliance 20.

Referring briefly back to the formation of the appliance, it is to be appreciated that when a set of appliances 20 are formed, so that intermediate post-alignment positions of a misaligned tooth comes into play, said intermediate positions will be taken into account when forming the various appliances 20, i.e. the model used for forming the appliances 20 will be manipulated after forming of each appliance 20.

Although the example herein described and illustrated pertains particularly to lower anterior teeth, it should be appreciated that it can be applied to correct alignment of any tooth in either the upper or lower arch. Likewise, although in this example the misaligned tooth 32 is moved in a facial or outward direction, it should be appreciated that the appliance 20 can equally advantageously be employed to move misaligned teeth in a lingual or inward direction. In fact, misaligned teeth in an arch can simultaneously respectively be moved in a facial and a lingual direction. It should further be appreciated that although the illustrated example of the embodiment deals with translational movement of a misaligned tooth, i.e. movement in a lingual or facial direction, an appliance of the type described can equally advantageously be employed to effect rotational movement of a tooth, i.e. movement about a longitudinal axis of the tooth. Likewise, the appliance 20 can be used laterally to move a tooth, or to effect a combination of one or more of translational, rotational and lateral movement.

Because of the particular construction of the appliance herein described, significant movement of misaligned teeth can be obtained by use of a single appliance. Furthermore, because the appliance properly seats on the teeth in an arch, correction forces which will be applied by the appliance on the teeth in the arch can be predicted, thereby reducing the risk of damage to the appliance and/or the gum tissue of a patient due to excessive forces.

Although the invention has been described with reference to preferred embodiments, it would be appreciated by persons skilled in the art that the invention may be embodied in many other forms.

The invention claimed is:

1. A dental appliance for correcting tooth alignment, the appliance comprising:
   a body for seating on an arch of teeth, the body having a lingual wall configured to confront lingual surfaces of a patient's teeth, a facial wall configured to confront facial surfaces of the patient's teeth, and a connecting wall connecting the lingual wall and the facial wall, wherein:
   (i) at least one of the lingual wall and the facial wall is elastically deformable from a pre-seated condition in which the body is not seated on the arch of teeth into a seated condition in which the body is seated on the arch of teeth, the lingual wall and the facial wall being separated from each other a first distance at corresponding first ends connected to the connecting wall and separated from each other a second distance less than the first distance at corresponding second ends opposite the first ends when the at least one elastically deformable wall is in the pre-seated condition,
   (ii) the separation of the lingual wall from the facial wall results in a recess to receive the teeth such that, when the body is in the pre-seated condition, the recess includes accommodation for a misaligned tooth in a desired post-alignment position and for only a distal tip of the misaligned tooth in a pre-alignment position, and
   (iii) the body applies, when seated on the arch of teeth and by virtue of the elastic deformation of the at least one elastically deformable wall, a correction force on one or more misaligned teeth, the correction force being applied by an interior face of the at least one elastically deformable wall to a base of the crown at a gum margin of the one or more misaligned teeth, in a direction in which each of the one or more misaligned teeth is to be moved to correct its alignment.

2. The dental appliance as claimed in claim 1, wherein, when the body is in its seated condition its recess provides for simultaneous accommodation of a misaligned tooth in its required post-alignment position and in its pre-alignment position.

3. The dental appliance as claimed in claim 2, wherein the body of the appliance is constructed such that when it is in its seated condition, its recess provides for simultaneous accommodation of the entire crown of each misaligned tooth both in its pre-alignment position and its required post-alignment position.

4. The dental appliance as claimed in claim 1, wherein the appliance is removable.

5. The dental appliance as claimed in claim 1, wherein the appliance is at least partially transparent.

6. The dental appliance as claimed in claim 5, wherein the entire appliance is transparent.

7. The dental appliance as claimed in claim 1, wherein the appliance is constructed from a material suitable for intraoral use.

8. The dental appliance as claimed in claim 1, wherein the appliance is constructed such that the recess of its body accommodates at least a majority of the teeth in an arch.

9. The dental appliance as claimed in claim 8, wherein the appliance is constructed such that the recess of its body accommodates all of the teeth in an arch.

10. The dental appliance as claimed in claim 1, wherein the recess of the body is shaped such that when the body is in both its pre-seated condition and its seated condition, it accommodates each tooth whose alignment does not require correction in the current position of the tooth.

11. The dental appliance as claimed in claim 1, wherein the body of the appliance is generally in the form of a shell which, when seen in outline in plan view, follows the general outline of an arch of teeth.

12. The dental appliance as claimed in claim 11, wherein the body is in the form of a relatively thin-walled shell, following the contours of the teeth in an arch.

13. The dental appliance as claimed in claim 1, wherein the body of the appliance, when seen in cross-section, is roughly U-shaped, when to be used in relation to an upper arch of teeth, or roughly inverted U-shaped, when to be used in relation to a lower arch of teeth.

14. The dental appliance as claimed in claim 1, wherein, when the body of the appliance is deformed from its pre-seated condition to its seated condition, a part or parts of the lingual wall and/or the facial wall of the body associated with misaligned teeth will be elastically deformed away from the other one of the lingual wall and the facial wall about the connecting wall.

15. The dental appliance as claimed in claim 14, wherein the part of the connecting wall associated with each misaligned tooth is wide enough simultaneously to cover the tip of each misaligned tooth when the tooth is in its pre-alignment position and its required post-alignment position, thereby permitting proper seating of the appliance on an arch of teeth including misaligned teeth.

16. A dental appliance for correcting tooth alignment, the appliance comprising:
an elastically deformable body having a lingual wall configured to confront lingual surfaces of a patient's teeth, a facial wall configured to confront facial surfaces of the patient's teeth, and a connecting wall connecting the lingual wall and the facial wall,
wherein the lingual wall and the facial wall are separated from each other a first distance at corresponding first ends connected to the connecting wall and separated from each other a second distance less than the first distance at corresponding second ends opposite the first ends when the at least one elastically deformable wall is in a pre-seated condition, with at least one of the lingual wall and the facial wall being elastically deformable away from the other one of the lingual wall and the facial wall to permit seating of the body on an arch of teeth having one or more misaligned teeth with the teeth in the arch to be received in a recess defined by the separation between the two walls, so that in use the at least one elastically deformed wall of the body applies a correction force on at least one misaligned tooth in the arch in a direction towards the other one of the lingual wall and the facial wall, said deformable portion of the body being constructed such that a correction force applied thereby on a base of the crown at a gum margin of said misaligned tooth exceeds a force applied on an upper part of the crown of the misaligned tooth, wherein the recess includes accommodation for a misaligned tooth in a desired post-alignment position and for only a distal tip of the misaligned tooth in a pre-alignment position when the body is in the pre-seated condition.

17. A dental appliance for correcting tooth alignment, the appliance comprising:
a body for seating on an arch of teeth having one or more misaligned teeth, the body having a lingual wall configured to confront lingual surfaces of a patient's teeth, a facial wall configured to confront facial surfaces of the patient's teeth, and a connecting wall connecting the lingual wall and the facial wall, wherein:
(i) at least one of the lingual wall and the facial wall is constructed to be elastically deformed from a pre-seated condition in which the body is not seated on the arch of teeth into a seated condition in which the body is seated on the arch of teeth, the lingual wall and the facial wall being separated from each other a first distance at corresponding first ends connected to the connecting wall and separated from each other a second distance less than the first distance at corresponding second ends opposite the first ends when the at least one elastically deformable wall is in the pre-seated condition,
(ii) the separation of the lingual wall from the facial wall results in a recess to receive the arch of teeth such that, when the body is in the pre-seated condition, the recess includes accommodation for the one or more misaligned teeth in a desired post-alignment position and for only a distal tip of the one or more misaligned teeth in a pre-alignment position,
(iii) the body applies, when seated on the arch of teeth and by virtue of the elastic deformation, a correction force by an interior face of the at least one elastically deformable wall to a base of the crown at a gum margin of at least one of the one or more misaligned teeth in the arch to move the at least one of the one or more misaligned teeth tooth, and
(iv) the dental appliance is being constructed for effecting movement of up to about 1 mm of the at least one of the one or more misaligned teeth.

18. A dental appliance for correcting tooth alignment, the appliance comprising:
an elastically deformable body for seating on an arch of teeth having at least one misaligned tooth, the body having a lingual wall configured to confront lingual surfaces of a patient's teeth, a facial wall configured to confront facial surfaces of the patient's teeth, and a connecting wall connecting the lingual wall and the facial wall, wherein:
(i) at least one of the lingual wall and the facial wall is constructed to be elastically deformed from a pre-seated condition in which the body is not seated on the arch of teeth into a seated condition in which the body is seated on an arch of teeth, the lingual wall and the facial wall being separated from each other a first distance at corresponding first ends connected to the connecting wall and separated from each other a second distance less than the first distance at corresponding second ends opposite the first ends when the at least one elastically deformable wall is in the pre-seated condition,
(ii) the body applies, when seated on the arch and by virtue of said elastic deformation, a greater correction force by an interior face of the at least one elastically deformable wall on a base of the crown at a gum margin of at least one misaligned tooth in the arch than on an upper part of the crown of the misaligned tooth, and (iii) the separation of the lingual wall from the facial wall results in a recess to receive the arch of teeth such that, when the body is in the pre-seated condition, the recess includes accommodation for the at least one misaligned tooth in a desired post-alignment position and for only a distal tip of the at least one misaligned tooth in a pre-alignment position.

19. A set of appliances for correcting tooth alignment, the set comprising:

a plurality of the appliances, each appliance including a body for seating on an arch of teeth, the body having a lingual wall configured to confront lingual surfaces of a patient's teeth, a facial wall configured to confront facial surfaces of the patient's teeth, and a connecting wall connecting the lingual wall and the facial wall, wherein:

(i) at least one of the lingual wall and the facial wall is elastically deformable from a pre-seated condition in which the body is not seated on the arch of teeth into a seated condition in which the body is seated on the arch of teeth, the lingual wall and the facial wall being separated from each other a first distance at corresponding first ends connected to the connecting wall and separated from each other a second distance less than the first distance at corresponding second ends opposite the first ends when the at least one elastically deformable wall is in the pre-seated condition, (ii) the body applies, when seated on the arch of teeth and by virtue of the elastic deformation of the at least one deformable wall, a correction force on one or more misaligned teeth, the correction force being applied by an interior face of at least one elastically deformable wall to a base of the crown at a gum margin of the one or more misaligned teeth, in a direction in which each of the one or more misaligned teeth is to be moved to correct its alignment, and (iii) the separation of the lingual wall from the facial wall results in a recess for receiving teeth, such that, when the body is in its pre-seated condition, the recess includes accommodation for a misaligned tooth in a desired post-alignment position and for only a distal tip part of the misaligned tooth in a pre-alignment position.

20. The set of appliances as claimed in claim 19, wherein the appliances of the set are shaped such that the pre-seated condition of the body of one appliance, as far as accommodation of a lower part or base of the crown of each misaligned tooth by its recess is concerned, substantially corresponds with the seated condition of the body of the succeeding appliance in the set.

21. A method of correcting tooth alignment, the method comprising:

applying a correction force by means of an elastically deformable tooth alignment appliance on a base of the crown at a gum margin of a misaligned tooth, the elastically deformable tooth alignment appliance including a body for seating on an arch of teeth, the body having a lingual wall configured to confront lingual surfaces of a patient's teeth, a facial wall configured to confront facial surfaces of the patient's teeth, and a connecting wall connecting the lingual wall and the facial wall, wherein:

(i) at least one of the lingual wall and the facial wall is elastically deformable from a pre-seated condition in which the body is not seated on the arch of teeth into a seated condition in which the body is seated on the arch of teeth, the lingual wall and the facial wall being separated from each other a first distance at corresponding first ends connected to the connecting wall and separated from each other a second distance less than the first distance at corresponding second ends opposite the first ends when the at least one elastically deformable wall is in the pre-seated condition, (ii) the separation of the lingual wall from the facial wall results in a recess to receive the arch of teeth such that, when the body is in the pre-seated condition, the recess includes accommodation for the misaligned tooth in a desired post-alignment position and for only a distal tip of the misaligned tooth in a pre-alignment position, and (iii) the body applies, when seated on the arch of teeth and by virtue of the elastic deformation of the at least one elastically deformable wall, the correction force by an interior face of the at least one elastically deformable wall in a direction in which the misaligned tooth is to be moved to correct its alignment.

22. The method as claimed in claim 21, wherein the method includes simultaneously correcting alignment of more than one tooth.

* * * * *